(12) United States Patent
Tsuchida et al.

(10) Patent No.: US 9,732,363 B2
(45) Date of Patent: Aug. 15, 2017

(54) GROWTH METHOD FOR MICROBE AND BIOETHANOL PRODUCTION METHOD

(71) Applicant: HONDA MOTOR CO., LTD., Tokyo (JP)

(72) Inventors: Yoshiki Tsuchida, Saitama (JP); Norihiko Tsukagoshi, Saitama (JP); Masaki Ueyama, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 108 days.

(21) Appl. No.: 14/643,149

(22) Filed: Mar. 10, 2015

(65) Prior Publication Data

US 2015/0259706 A1 Sep. 17, 2015

(30) Foreign Application Priority Data

Mar. 14, 2014 (JP) .................. 2014-051930
Mar. 14, 2014 (JP) .................. 2014-051931

(51) Int. Cl.
*C12P 7/06* (2006.01)
*C12N 1/22* (2006.01)
*C12P 7/10* (2006.01)

(52) U.S. Cl.
CPC ............... *C12P 7/065* (2013.01); *C12N 1/22* (2013.01); *C12P 7/10* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| 2011/0065785 A1* | 3/2011 | Larsen ................. C12P 7/06 514/461 |
| 2011/0165639 A1* | 7/2011 | Ascon .................. C12M 21/12 435/134 |

FOREIGN PATENT DOCUMENTS

| JP | 2012-170443 | 9/2012 |
| WO | 2012/118171 A1 | 9/2012 |

OTHER PUBLICATIONS

Lennartsson et al., Integration of the first and second generation bioethanol processes and the importance of by-products, Bioresource Technology 165, Available online Feb. 8, 2014, pp. 3-8.*
Sakai et al., Effect of Lignocellulose-Derived Inhibitors on Growth of and Ethanol Production by Growth-Arrested Corynebacterium glutamicim R, Applied and Environmental Microbiology, vol. 73, No. 7, Apr. 2007, pp. 2349-2353.*

* cited by examiner

*Primary Examiner* — Karen Cochrane Carlson
*Assistant Examiner* — Jennifer M. H. Tichy
(74) *Attorney, Agent, or Firm* — Rankin, Hill & Clark LLP

(57) ABSTRACT

The present invention provides a growth method for a microbe which can enhance the growth of the microbe without removing growth inhibitors from a saccharified solution. The growth method for a microbe comprises the steps of: obtaining a mixed saccharified solution by diluting the saccharified solution containing a growth inhibitor which inhibits the growth of the microbe with a sugar solution having a smaller growth inhibitor concentration than that of the saccharified solution such that the growth inhibitor concentration is decreased; and allowing the microbe to grow by adding the microbe to the mixed saccharified solution.

31 Claims, 7 Drawing Sheets

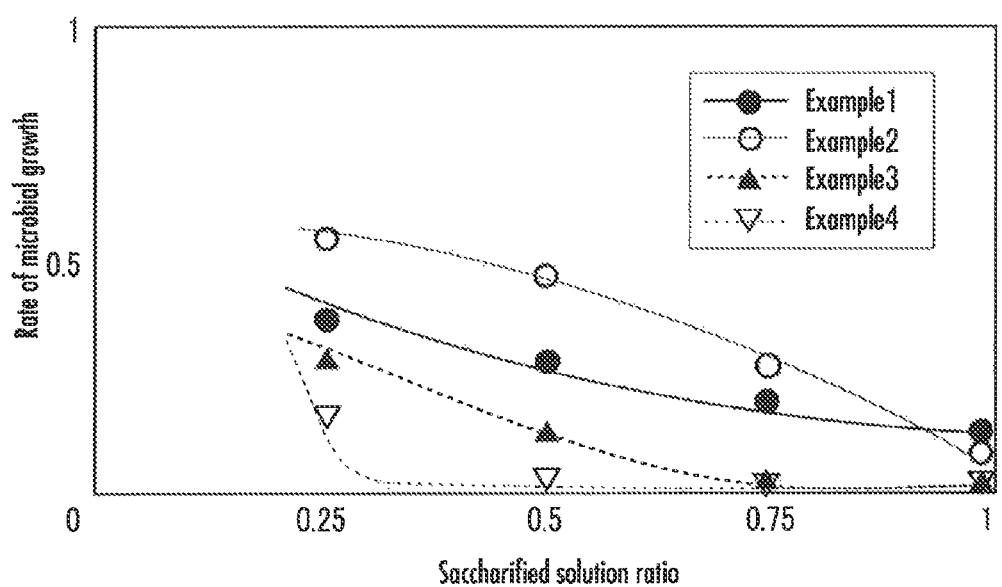

GROWTH METHOD FOR MICROBE AND BIOETHANOL PRODUCTION METHOD

BACKGROUND OF THE INVENTION

Field of the Invention

The present invention relates to a growth method for a microbe in a saccharified solution containing a saccharification product, and a bioethanol production method which forms ethanol by fermenting a saccharified solution with a microbe allowed to grow by the growth method.

Description of the Related Art

In recent years, there has been a demand for reduction in carbon dioxide emission, which is considered to be a cause of global warming, and use of biomass-derived diesel fuel or blended fuel of liquid hydrocarbon (e.g., gasoline) and biomass-derived ethanol as automobile fuel has been studied. Ethanol obtained by the fermentation of plant materials such as crops including sugarcane and corn can be used as the ethanol.

The amount of carbon dioxide emitted upon combustion of the ethanol obtained from such plant materials is equal to that absorbed by the raw material plant itself, because the plant itself has already absorbed carbon dioxide through photosynthesis. This means that the carbon dioxide emission is theoretically zero-sum, i.e., so-called carbon neutral effect can be obtained.

The crops such as sugarcane and corn are supposed to be food. In this respect, the problem is that the supply of these crops as food is decreased if they are consumed in large amounts as raw materials for ethanol.

Accordingly, techniques have been studied to produce ethanol using lignocellulosic biomass (hereinafter, also simply referred to as biomass), which is not used for food, instead of the crops (e.g., sugarcane and corn) as raw materials. The lignocellulosic biomass contains cellulose and hemicellulose (hereinafter, also collectively referred to as celluloses). These celluloses can be degraded with saccharifying enzymes into sugars, such as glucose or xylose, and the obtained sugars can be fermented to obtain ethanol.

Examples of the lignocellulosic biomass can include wood, rice straw, wheat straw, bagasse, bamboo, stalks, leaves, and cobs of corn, pulp, and wastes resulting therefrom, for example, waste paper.

The lignocellulosic biomass has hemicellulose and lignin as main constituents, in addition to cellulose. Since cellulose and hemicellulose are usually bound tightly to lignin, these celluloses are difficult to saccharify through direct reaction.

Thus, the lignocellulosic biomass-derived ethanol has heretofore been produced as follows: first, by the pretreatment of lignocellulosic biomass, lignin is dissociated from the lignocellulosic biomass or the lignocellulosic biomass is swollen to obtain a pretreatment product.

In the present specification, the dissociation refers to the cleavage of at least some bonds of sites at which lignin is bound to cellulose or hemicellulose in the lignocellulosic biomass. The swelling refers to the entrance of a liquid to form gaps in cellulose or hemicellulose constituting crystalline cellulose or gaps in cellulose fibers, resulting in expansion.

Next, a saccharified solution is obtained by saccharifying the pretreatment product using the saccharifying enzyme. Subsequently, a microbe added to the saccharified solution is allowed to grow so that the saccharified solution is fermented, thereby forming ethanol. Bioethanol is produced by distilling the obtained ethanol solution. In this respect, the problem is that low fermentation efficiency in the fermentation requires large energy for the distillation and increases cost.

To solve the problem, a technique of elevating a sugar concentration by mixing molasses of sugarcane with the saccharified solution, and fermenting the obtained mixed solution has been proposed (see Japanese Patent Laid-Open No. 2012-170443). According to the conventional technique, fermentation efficiency in the fermentation can be improved.

However, the problem of the conventional technique is also that the fermentation efficiency cannot be improved in some cases.

The present inventors have studied a reason why the fermentation efficiency may not be improved in the conventional technique. As a result, it has been found that the saccharified solution contains compounds, such as acetic acid, formic acid, and p-coumaric acid, formed as byproducts during the pretreatment and the saccharification, and the growth of the microbe is inhibited by the compounds during the fermentation. In the present application, such a compound which inhibits the growth of the microbe is referred to as a "growth inhibitor".

The growth inhibitor inhibits the growth of the microbe in the case where bioethanol is formed by fermenting the saccharified solution as well as in the case where useful materials such as biodiesel fuel or the like are obtained.

Thus, to reduce the influence of the growth inhibitor, a technique of removing the growth inhibitor from the mixed solution by filtering a mixed solution in which the saccharified solution is mixed with the molasses through a nanofiltration membrane or a reverse osmosis membrane has been proposed (see International Publication No. WO 2012/118171).

However, the filtration of the saccharified solution using the nanofiltration membrane or the reverse osmosis membrane requires a filtration step. This is inconvenient because production steps are complicated while a time required for bioethanol production is increased, and furthermore, a facility for filtration is necessary.

SUMMARY OF THE INVENTION

An object of the present invention is to solve such inconvenience and provide a growth method for a microbe which can enhance the growth of the microbe without removing growth inhibitors from a saccharified solution, and a bioethanol production method which can avoid inhibiting the growth of the microbe during fermentation. The removal means that the growth inhibitors contained in the saccharified solution are eliminated or rendered invalid by filtration, neutralization, adsorption, or the like.

The present invention provides a growth method for a microbe in a saccharified solution containing a saccharification product, comprising steps of: obtaining a mixed saccharified solution by diluting the saccharified solution containing a growth inhibitor which inhibits the growth of the microbe with a sugar solution having a smaller growth inhibitor concentration than that of the saccharified solution such that the growth inhibitor concentration is decreased; and allowing the microbe to grow by adding the microbe to the mixed saccharified solution.

In the present application, the "saccharified solution" means a mixture of a saccharification product with a liquid as a solvent. Its form may be slurry or may be liquid.

In the growth method for a microbe of the present invention, first, a mixed saccharified solution having a decreased growth inhibitor concentration is obtained by diluting the saccharified solution containing a growth inhibitor which inhibits the growth of the microbe with a sugar solution having a smaller growth inhibitor concentration than that of the saccharified solution. Subsequently, the microbe is allowed to grow by adding the microbe to the mixed saccharified solution. Since the mixed saccharified solution has a decreased growth inhibitor concentration, the growth of the microbe can be prevented from being inhibited by the growth inhibitor.

Thus, the growth method for a microbe of the present invention can enhance the growth of the microbe without removing growth inhibitors.

In the growth method for a microbe of the present invention, for example, a saccharified solution containing a saccharification product obtained by saccharifying, with a saccharifying enzyme, a pretreatment product resulting from the pretreatment of lignocellulosic biomass can be used as the saccharified solution.

In the growth method for a microbe of the present invention, for example, one or more microbes selected from a group consisting of prokaryotic microorganisms including a bacterium, and eukaryotic microorganisms including a fungus and an alga can be used as the microbe.

The bacterium is, for example, one or more microbes selected from a group consisting of *Zymomonas mobilis, Zymobacter palmae, Clostridium* sp. (*Clostridium phytofermentans, Clostridium thermocellum, Clostridium beijerinckii, Clostridium acetobutylicum*), *Moorella thermoacetica, Escherichia coli, Klebsiella oxytoca, Thermoanaerobacterium saccharolyticum, Bacillus subtilis, Corynebacterium glutamicum*.

The fungus is, for example, one or more microbes selected from the group consisting of: one or more yeasts selected from the group consisting of *Saccharomyces* sp. (*Saccharomyces cerevisiae, Saccharomyces monacensis, Saccharomyces bayanus, Saccharomyces pastorianus, Saccharomyces carlsbergensis, Saccharomyces pombe*), *Kluyveromyces* sp. (*Kluyveromyces marxiamus, Kluyveromyces lactis, Kluyveromyces fragilis*), *Pichia stipitis, Candida shehatae, Candida tropicalis, Meyerozyma guilliermondii, Rhodosporidium toruloides, Lipomyces starkyei, Yarrowia lipolytica, Sporotrichum thermophile, Myceliophthora thermophila, Neurospora crassa, Cryptococcus curvatus*; and a filamentous fungus.

The alga is, for example, one or more microbes selected from a group consisting of *Aurantiochytrium, Nannochloropsis, Schizochytrium, Nannochloris, Stichococcus, Neochloris oleoabundans, Chlorella, Dunaliella, Botryococcus braunii, Scenedesmus, Hantzschia*.

The growth method for a microbe of the present invention can be further applied to a bioethanol production method which forms ethanol by fermenting a mixed saccharified solution with the microbe thus allowed to grow.

Specifically, the bioethanol production method of the present invention is a bioethanol production method of saccharifying, with a saccharifying enzyme, a pretreatment product resulting from the pretreatment of lignocellulosic biomass, and fermenting the obtained saccharified solution with a microbe to form ethanol, the method comprising steps of: obtaining a mixed saccharified solution by diluting the saccharified solution containing a growth inhibitor which inhibits the growth of the microbe with a sugar solution having a smaller growth inhibitor concentration than that of the saccharified solution such that the growth inhibitor concentration is decreased; and fermenting the mixed saccharified solution with the microbe to form ethanol.

In the bioethanol production method of the present invention, first, a pretreatment product resulting from pretreatment of lignocellulosic biomass is saccharified with a saccharifying enzyme, and a mixed saccharified solution having a decreased growth inhibitor concentration is obtained by diluting the obtained saccharified solution with a sugar solution having a smaller growth inhibitor concentration than that of the saccharified solution. Subsequently, the mixed saccharified solution is fermented with the microbe to form ethanol. Since the mixed saccharified solution has a decreased growth inhibitor concentration during the fermentation, the growth of the microbe can be prevented from being inhibited by the growth inhibitor.

Thus, the bioethanol production method of the present invention can avoid inhibiting the growth of the microbe during fermentation, without removing growth inhibitors. As a result, the bioethanol production method of the present invention can improve fermentation efficiency.

In the bioethanol production method of the present invention, for example, one or more microbes selected from a group consisting of a yeast, *Zymomonas, Zymobacter, Corynebacterium*, and *Escherichia coli* can be used as the microbe.

In the growth method for a microbe or the bioethanol production method of the present invention, examples of the growth inhibitor can include one or more compounds selected from a group consisting of an organic acid, a compound having an aldehyde group, a compound having a ketone group, and a compound having a phenol group, melanoidin.

The organic acid is, for example, one or more compounds selected from a group consisting of acetic acid, formic acid, p-coumaric acid, ferulic acid, and benzoic acid. The compound having an aldehyde group is, for example, one or more compounds selected from a group consisting of furfural, 5-hydroxymethylfurfural, vanillin, syringaldehyde, and 4-hydroxyacetophenone. The compound having a phenol group is, for example, one or more compounds selected from a group consisting of phenol and guaiacol.

In the growth method for a microbe or the bioethanol production method of the present invention, it is preferred that the saccharified solution should contain at least acetic acid as the growth inhibitor, and the step of obtaining a mixed saccharified solution can comprise diluting the saccharified solution such that the concentration of an undissociated form of the acetic acid is 700 mg/L or lower. Alternatively, it is preferred that the saccharified solution should contain at least furfural as the growth inhibitor, and the step of obtaining a mixed saccharified solution can comprise diluting the saccharified solution such that the concentration of the furfural is 700 mg/L or lower. Alternatively, it is preferred that the saccharified solution should contain at least p-coumaric acid as the growth inhibitor, and the step of obtaining a mixed saccharified solution can comprise diluting the saccharified solution such that the concentration of the p-coumaric acid is 500 mg/L or lower.

When the mixed saccharified solution has each growth inhibitor concentration within the range, the growth of the microbe can be further enhanced. In the case where each growth inhibitor concentration exceeds the range, the sufficient growth of the microbe may not be achieved.

In the growth method for a microbe or the bioethanol production method of the present invention, for example, one or more types of liquids selected from a group consisting of molasses of sugarcane, juice of sugarcane, a concentrate of the juice of sugarcane, a liquid of saccharified rice, a liquid of saccharified wheat, and a liquid of saccharified corn can be used as the sugar solution. The molasses is a residual liquid that remains after crystallization of sugar from juice of sugarcane, and is also called syrup. Hereinafter, the molasses of sugarcane is also simply referred to as "molasses". The growth inhibitor concentration can be decreased at low cost by using the above liquids as the sugar solution.

In the growth method for a microbe or the bioethanol production method of the present invention, it is preferred that the step of allowing the microbe to grow can comprise adjusting a pH of the mixed saccharified solution to a range of 4 to 7 before adding the microbe to the mixed saccharified solution.

In the growth method for a microbe or the bioethanol production method of the present invention, a mixed saccharified solution having a saccharified solution ratio that can enhance the growth of the microbe can be obtained as described below. In the present specification, the "saccharified solution ratio" means the ratio of the mass of the saccharified solution with respect to the total mass of a mixed saccharified solution when the mixed saccharified solution is obtained by diluting the saccharified solution with the sugar solution. In this method, the saccharified solution ratio is determined by focusing on the concentration of growth inhibitor(s) contained in the saccharified solution. First, a method focusing on one type of growth inhibitor will be described.

First, in a first step, a plurality of culture media is prepared in which a sugar solution for testing is supplemented with the growth inhibitor at respective different growth inhibitor concentrations. Then, the microbe is cultured using the plurality of culture media, and the number of grown microbes at the growth inhibitor concentration contained in each culture medium is measured.

Subsequently, in a second step, the microbe is cultured using the sugar solution for testing unsupplemented with the growth inhibitor as a culture medium, and the number of grown microbes in the unsupplemented sugar solution for testing is measured as the reference number of grown microbes.

Subsequently, in a third step, the rate of microbial growth at the growth inhibitor concentration in each culture medium is calculated by dividing the number of grown microbes at each growth inhibitor concentration obtained in the first step by the reference number of grown microbes obtained in the second step.

Subsequently, in a fourth step, a first growth inhibition curve is prepared from the relationship between the growth inhibitor concentration of each culture medium and the rate of microbial growth obtained in the third step.

Subsequently, in a fifth step, a growth inhibitor concentration of the saccharified solution for use in the growth of the microbe is measured.

Subsequently, in a sixth step, the rate of microbial growth corresponding to the growth inhibitor concentration of the saccharified solution obtained in the fifth step is determined from the first growth inhibition curve obtained in the fourth step.

Subsequently, in a seventh step, first, the saccharified solution ratio of the saccharified solution in an undiluted state is defined as 1. Next, as to each of mixed saccharified solutions in which the undiluted saccharified solution is diluted with the sugar solution for use in the growth of the microbe in respective different amounts, the rate of microbial growth corresponding to the saccharified solution ratio of each mixed saccharified solution is determined from the first growth inhibition curve obtained in the fourth step. In this context, the growth inhibitor concentration of the sugar solution is regarded as being zero, because it is much smaller than the growth inhibitor concentration of the saccharified solution and is substantially ignorable.

Subsequently, in an eighth step, a second growth inhibition curve is prepared from the relationship between the saccharified solution ratio of each mixed saccharified solution and the rate of microbial growth obtained in the seventh step.

Subsequently, in a ninth step, a saccharified solution ratio corresponding to the desired rate of microbial growth is determined from the second growth inhibition curve obtained in the eighth step.

Subsequently, in a tenth step, the mixed saccharified solution is obtained by diluting the saccharified solution with the sugar solution for use in the growth of the microbe such that the saccharified solution ratio obtained in the ninth step is achieved.

In this way, the mixed saccharified solution that can enhance the growth of the microbe can be obtained without removing the growth inhibitor.

According to the method of determining the saccharified solution ratio by focusing on the concentration of the growth inhibitor contained in the saccharified solution, the dilution can be carried out by focusing on the growth inhibitor, which has the largest influence on the phenomenon where the growth of the microbe is inhibited.

Also, the saccharified solution ratio can be determined by focusing on a plurality of growth inhibitors contained in the saccharified solution, as described below.

First, in a first step, a plurality of culture media is prepared in which, with respect to each growth inhibitor of a plurality of growth inhibitors contained in the saccharified solution for use in the growth of the microbe, a sugar solution for testing is supplemented with the growth inhibitor at respective different growth inhibitor concentrations. Then, the microbe is cultured using the plurality of culture media with respect to each growth inhibitor, and the number of grown microbes at the growth inhibitor concentration contained in each culture medium with respect to each growth inhibitor is measured.

Subsequently, in a second step, the microbe is cultured using the sugar solution for testing unsupplemented with each growth inhibitor as a culture medium, and the number of grown microbes in the unsupplemented sugar solution for testing is measured to prepare the reference number of grown microbes.

Subsequently, in a third step, the rate of microbial growth at the growth inhibitor concentration in each culture medium is calculated with respect to each growth inhibitor by dividing the number of grown microbes at the growth inhibitor concentration with respect to each growth inhibitor obtained in the first step by the reference number of grown microbes obtained in the second step.

Subsequently, in a fourth step, a first growth inhibition curve is prepared with respect to each growth inhibitor from the relationship between the growth inhibitor concentration of each culture medium and the rate of microbial growth with respect to each growth inhibitor obtained in the third step.

Subsequently, in a fifth step, each growth inhibitor concentration of the saccharified solution is measured.

Subsequently, in a sixth step, the rate of microbial growth corresponding to the growth inhibitor concentration of the saccharified solution with respect to each growth inhibitor obtained in the fifth step is determined from the first growth inhibition curve with respect to each growth inhibitor obtained in the fourth step.

Subsequently, in a seventh step, first, the saccharified solution ratio of the saccharified solution in an undiluted state is defined as 1. Next, as to each of mixed saccharified solutions in which the undiluted saccharified solution is diluted with the sugar solution for use in the growth of the microbe in respective different amounts, the rate of microbial growth corresponding to the saccharified solution ratio of each mixed saccharified solution is determined from the first growth inhibition curve with respect to each growth inhibitor obtained in the fourth step. Then, the rate of microbial growth corresponding to the saccharified solution ratio of each mixed saccharified solution is calculated by multiplying the respective rates of microbial growth against the growth inhibitors in mixed saccharified solutions having the same saccharified solution ratio.

Subsequently, in an eighth step, a second growth inhibition curve is prepared from the relationship between the saccharified solution ratio of each mixed saccharified solution and the rate of microbial growth obtained in the seventh step.

Subsequently, in a ninth step, a saccharified solution ratio corresponding to the desired rate of microbial growth is determined from the second growth inhibition curve obtained in the eighth step.

Subsequently, in a tenth step, the mixed saccharified solution is obtained by diluting the saccharified solution with the sugar solution for use in the growth of the microbe such that the saccharified solution ratio obtained in the ninth step is achieved.

In this way, the mixed saccharified solution that can enhance the growth of the microbe can be obtained without removing the growth inhibitors.

According to the method of determining the saccharified solution ratio by focusing on plural types of growth inhibitors, the saccharified solution ratio can be determined more accurately as compared with the method focusing on only one type of growth inhibitor.

In these two methods, the growth inhibitor concentration of the sugar solution is regarded as being zero, because it is much smaller than the growth inhibitor concentration of the saccharified solution and is substantially ignorable. Hence, the saccharified solution ratio is determined in consideration of only the growth inhibitor concentration of the saccharified solution. Thus, not only the growth inhibitor concentration of the saccharified solution but the growth inhibitor concentration of the sugar solution may be taken into consideration as described below.

First, a growth inhibitor concentration contained in the sugar solution is measured. Subsequently, in the first step, the sugar solution is used as the sugar solution for testing, and the microbe is cultured using a plurality of culture media in which the sugar solution is supplemented with the growth inhibitor. Then, the growth inhibitor concentration contained in the culture medium is defined as the sum of the growth inhibitor concentration measured as to the sugar solution and the concentration of the growth inhibitor added to the sugar solution as the sugar solution for testing. The number of grown microbes at each growth inhibitor concentration is measured.

Thereafter, the saccharified solution ratio is determined by carrying out the second step to the ninth step in the same way as the method of taking into consideration only the growth inhibitor concentration of the saccharified solution. Subsequently, in the tenth step, the mixed saccharified solution is obtained by diluting the saccharified solution with the sugar solution such that the saccharified solution ratio obtained in the ninth step is achieved.

According to the method of taking into consideration both of the growth inhibitor concentration of the saccharified solution and the growth inhibitor concentration of the sugar solution, the saccharified solution ratio can be determined further accurately as compared with the method of taking into consideration only the growth inhibitor concentration of the saccharified solution.

BRIEF DESCRIPTION OF THE DRAWINGS

FIG. 2A and FIG. 2B are graphs showing a growth inhibition curve $L_{\alpha 1}$, wherein FIG. 2A is a graph showing the status of preparation of the growth inhibition curve $L_{\alpha 1}$, and FIG. 2B is a graph showing the state of use of the growth inhibition curve $L_{\alpha 1}$;

FIG. 3A and FIG. 3B are graphs showing an overall growth inhibition curve $L_{\alpha 2}$, wherein FIG. 3A is a graph showing the status of preparation of the growth inhibition curve $L_{\alpha 2}$, and FIG. 3B is a graph showing the state of use of the growth inhibition curve $L_{\alpha 2}$;

FIG. 4A and FIG. 4B are graphs showing a growth inhibition curve $L_{\beta 1}$, wherein FIG. 4A is a graph showing the status of preparation of the growth inhibition curve $L_{\beta 1}$, and FIG. 4B is a graph showing the state of use of the growth inhibition curve $L_{\beta 1}$;

FIG. 5A and FIG. 5B are graphs showing an overall growth inhibition curve $L_{\alpha\beta 2}$, wherein FIG. 5A is a graph showing the status of preparation of the growth inhibition curve $L_{\alpha\beta 2}$, and FIG. 5B is a graph showing the state of use of the growth inhibition curve $L_{\alpha\beta 2}$;

FIG. 6 is a graph showing overall growth inhibition curves $L_{\alpha\beta \ldots \lambda 2}$ of Examples 1 to 4.

DETAILED DESCRIPTION OF THE PREFERRED EMBODIMENTS

Figure 1:
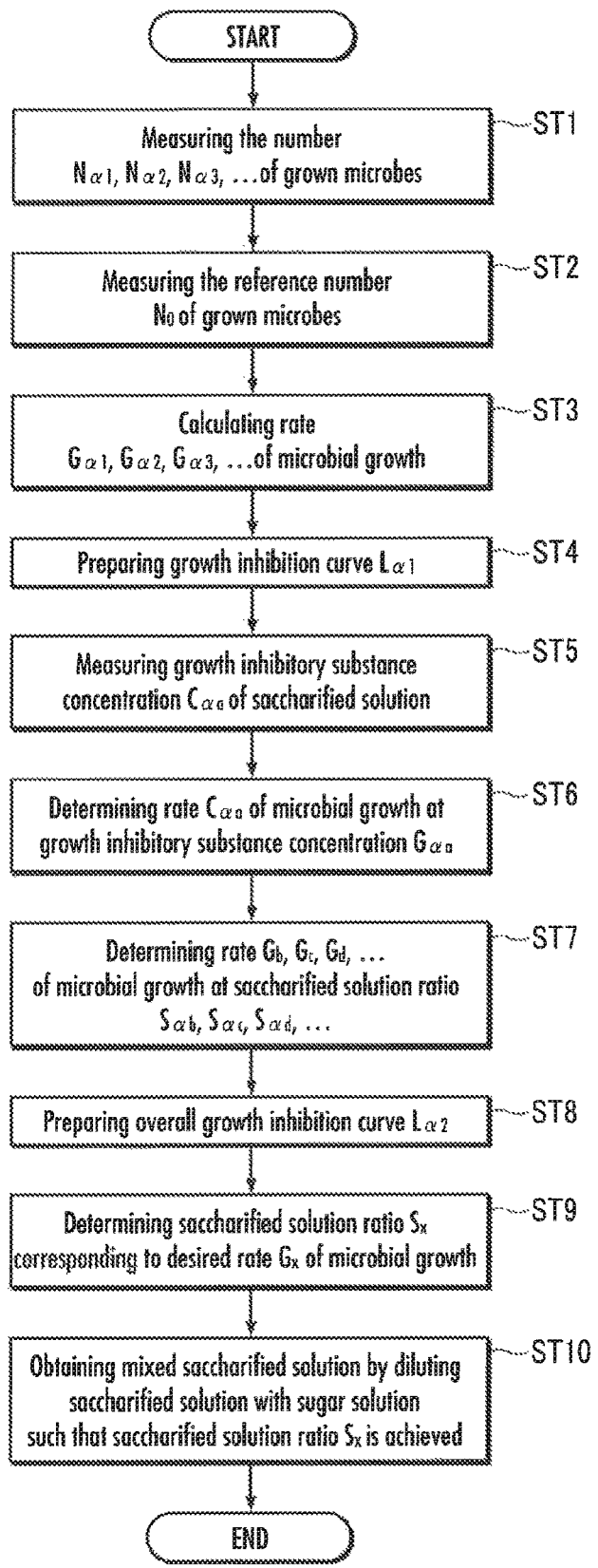
FIG. 1 is a flow chart showing a method of determining a saccharified solution ratio in a growth method for a microbe of a present embodiment.

Next, the embodiments of the present invention will be described further specifically.

First, a growth method for a microbe in a saccharified solution containing a saccharification product obtained by saccharifying, with a saccharifying enzyme, a pretreatment product resulting from the pretreatment of lignocellulosic biomass will be described.

The saccharified solution can be prepared as follows: first, by the pretreatment of lignocellulosic biomass, lignin is dissociated from the lignocellulosic biomass or the lignocellulosic biomass is swollen to obtain a pretreatment product. Examples of the lignocellulosic biomass can include wood, rice straw, wheat straw, bagasse, bamboo, stalks, leaves, and cobs of corn, pulp, and wastes resulting therefrom, for example, waste paper. Examples of the pretreatment can include wet milling, dry milling, blasting, steam treatment, and treatment with an acid or an alkali.

Next, a saccharified solution containing a saccharification product is obtained by saccharifying the obtained pretreatment product using a saccharifying enzyme. The saccharification can be carried out, for example, by adding the saccharifying enzyme and water to the pretreatment product, followed by stirring. The obtained saccharified solution is in a slurry state in which the saccharification product is mixed with water, and contains 20 to 300 g/L, preferably 50 to 200 g/L of sugar and contains growth inhibitors which inhibit the growth of the microbe as by-products.

Examples of the sugar can include glucose, xylose, and arabinose, or the like.

Examples of the growth inhibitor can include one or more compounds selected from a group consisting of: organic acids such as acetic acid, formic acid, p-coumaric acid, ferulic acid, and benzoic acid; compounds having an aldehyde group, such as furfural, 5-hydroxymethylfurfural (HMF), vanillin, syringaldehyde, and 4-hydroxyacetophenone; compounds having a phenol group, such as phenol and guaiacol; compounds having a ketone group; and melanoidin.

Next, a mixed saccharified solution is obtained by diluting the obtained saccharified solution with a sugar solution having a smaller growth inhibitor concentration than that of the saccharified solution such that the growth inhibitor concentration is decreased. For example, molasses formed as a by-product after concentration of juice of sugarcane and subsequent separation of crystals, juice of sugarcane, a concentrate of the juice of sugarcane, a liquid of saccharified rice, a liquid of saccharified wheat, or a liquid of saccharified corn can be used as the sugar solution. Particularly, in the case of using the molasses as the sugar solution, the growth inhibitor concentration can be decreased at low cost.

In the case where the mixed saccharified solution contains, for example, acetic acid, furfural, and p-coumaric acid as the growth inhibitor, the dilution is carried out such that the concentration of an undissociated form of the acetic acid is 700 mg/L or lower, the concentration of the furfural is 700 mg/L or lower, and the concentration of the p-coumaric acid is 500 mg/L or lower.

The obtained mixed saccharified solution has the growth inhibitor concentration lower than that of the saccharified solution by virtue of the dilution with the sugar solution.

Next, the pH of the mixed saccharified solution is adjusted, if necessary, to a predetermined pH. Then, the microbe is allowed to grow by adding the microbe to the mixed saccharified solution.

Examples of the microbe can include: prokaryotic microorganisms including a bacterium or the like; eukaryotic microorganisms including a fungus and an alga; and genetically modified forms of the microbe.

Examples of the bacteria can include *Zymomonas mobilis, Zymobacter palmae, Clostridium* sp. (*Clostridium phytofermentans, Clostridium thermocellum, Clostridium beijerinckii, Clostridium acetobutylicum*), *Moorella thermoacetica, Escherichia coli, Klebsiella oxytoca, Thermoanaerobacterium saccharolyticum, Bacillus subtilis, Corynebacterium glutamicum*, or the like.

Examples of the fungi can include: yeasts such as *Saccharomyces* sp. (*Saccharomyces cerevisiae, Saccharomyces monacensis, Saccharomyces bayanus, Saccharomyces pastorianus, Saccharomyces carlsbergensis, Saccharomyces pombe*), *Kluyveromyces* sp. (*Kluyveromyces marxiamus, Kluyveromyces lactis, Kluyveromyces fragilis*), *Pichia stipitis, Candida shehatae, Candida tropicalis, Meyerozyma guilliermondii, Rhodosporidium toruloides, Lipomyces starkyei, Yarrowia lipolytica, Sporotrichum thermophile, Myceliophthora thermophila, Neurospora crassa, Cryptococcus curvatus*, or the like; and filamentous fungi.

Examples of the algae can include *Aurantiochytrium, Nannochloropsis, Schizochytrium, Nannochloris, Stichococcus, Neochloris oleoabundans, Chlorella, Dunaliella, Botryococcus braunii, Scenedesmus, Hantzschia*, or the like.

Since the mixed saccharified solution has a decreased growth inhibitor concentration during the growth of the microbe using the mixed saccharified solution in which the saccharified solution is diluted with the sugar solution, the inhibition of the growth of the microbe by the growth inhibitor can be reduced.

Thus, the growth method for a microbe of the present embodiment can enhance the growth of the microbe without removing growth inhibitors by filtration, neutralization, adsorption, or the like.

According to the growth method for a microbe of the present embodiment, various products can be obtained in conjunction with the growth of the microbe. Examples of such products can include ethanol, which is a fermentation product. In the case where the microbe allowed to grow contains oil and fat, for example, fatty acid methyl ester for use as biodiesel can be obtained as the product.

The growth method for a microbe of the present embodiment can be further applied to a bioethanol production method which forms ethanol by fermenting a mixed saccharified solution with the microbe thus allowed to grow.

In the bioethanol production method of the present embodiment, first, a saccharified solution is obtained by saccharifying, with a saccharifying enzyme, a pretreatment product resulting from the pretreatment of lignocellulosic biomass. Next, a mixed saccharified solution is obtained by diluting the obtained saccharified solution with a sugar solution having a smaller growth inhibitor concentration than that of the saccharified solution such that the growth inhibitor concentration is decreased.

Then, ethanol is formed by fermenting the obtained mixed saccharified solution with the microbe. Examples of the microbe can include yeasts of the genus *Pichia* or other yeasts, *Zymomonas, Zymobacter, Corynebacterium, Escherichia coli*, and genetically modified forms of these microbes.

Since the mixed saccharified solution has a decreased growth inhibitor concentration, by virtue of the dilution, during fermentation of the mixed saccharified solution, the inhibition of the growth of the microbe by the growth inhibitor can be reduced.

Thus, the bioethanol production method of the present embodiment can avoid inhibiting the growth of the microbe during the fermentation and can improve fermentation efficiency, without removing growth inhibitors by filtration, neutralization, adsorption, or the like.

Next, referring to FIG. 1, a method of preparing a mixed saccharified solution having a saccharified solution ratio that can enhance the growth of the microbe in the growth method for a microbe or the bioethanol production method of the present embodiment will be described. The saccharified solution ratio can be determined by focusing on the concentration of one or more types of growth inhibitors of growth inhibitors $\alpha$, $\beta$, $\gamma$, $\delta$, $\epsilon$, . . . contained in the saccharified solution.

First, a method focusing on one type of growth inhibitor $\alpha$ among the growth inhibitors $\alpha$, $\beta$, $\gamma$, $\delta$, $\epsilon$, . . . contained in the saccharified solution will be described. A solution of saccharified rice straw is used as the saccharified solution, and molasses of sugarcane is used as the sugar solution. Although the molasses contains growth inhibitors, their concentrations can be regarded as being zero, because the concentrations are much smaller as compared with the solution of saccharified rice straw and are substantially ignorable.

First, a sugar solution for testing is prepared by dissolving glucose and xylose as sugars and peptone as a nutrient source for the microbe in water. The sugar solution for testing has a sugar concentration of 100 to 150 g/L, but contains no growth inhibitor, and is experimentally prepared for the sugar solution.

Next, a plurality of culture media are prepared by adding, for example, furfural, as the growth inhibitor α at respective different growth inhibitor concentrations $C_1$, $C_2$, $C_3$, . . . to the sugar solution for testing. Subsequently, the microbe is cultured using each culture medium thus obtained. The culture can be carried out, for example, by adding a yeast (*Meyerozyma guilliermondii*) as the microbe to the culture medium, followed by stirring or shaking at pH 4 to 7 at a temperature of 30° C. for 20 hours. The yeast can be added, for example, within a turbidity range of 0.05 to 5, to the culture medium.

Then, the number of grown microbes resulting from the culture is measured for each concentration $C_1$, $C_2$, $C_3$, . . . of the growth inhibitor α contained in each culture medium to prepare the number $N_{\alpha 1}$, $N_{\alpha 2}$, $N_{\alpha 3}$, . . . of grown microbes (step (hereinafter, abbreviated to ST) 1). The measurement of the number of the microbe can be carried out by measuring the turbidity of the culture medium. The turbidity is proportional to the number of the microbe.

Next, the microbe is cultured in totally the same way as in ST1 except that no growth inhibitor is added. The number of grown microbes in the unsupplemented sugar solution for testing is measured to prepare the reference number $N_0$ of grown microbes (ST2).

Next, the rate $G_{\alpha 1}$ ($G_{\alpha 1}=N_{\alpha 1}/N_0$), $G_{\alpha 2}$, $G_{\alpha 3}$, . . . of microbial growth at each growth inhibitor concentration $C_1$, $C_2$, $C_3$, . . . is calculated by dividing the number $N_{\alpha 1}$, $N_{\alpha e}$, $N_{\alpha 3}$, of grown microbes obtained in ST1 by the reference number $N_0$ of grown microbes obtained in ST2 (ST3).

Figure 2A:
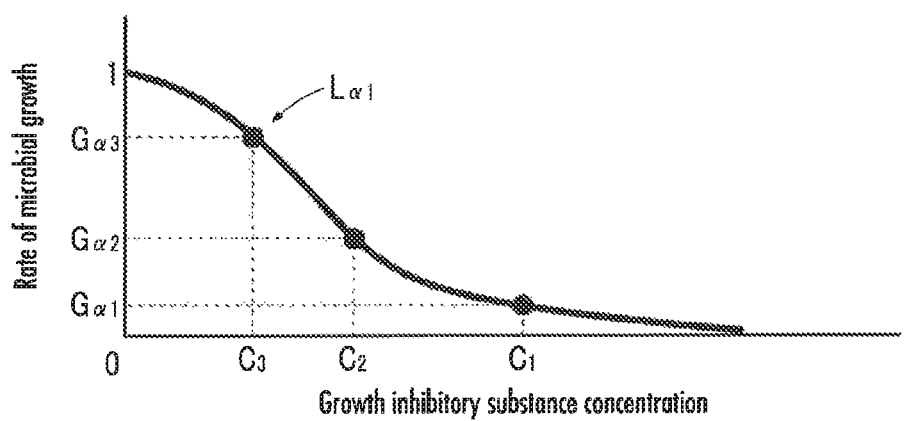

Next, a growth inhibition curve $L_{\alpha 1}$ as a first growth inhibition curve shown in FIG. 2A is prepared from the relationship between each growth inhibitor concentration $C_1$, $C_2$, $C_3$, . . . and the rate $G_{\alpha 1}$, $G_{\alpha 2}$, $G_{\alpha 3}$, . . . of microbial growth obtained in ST3 (ST4). In the graph shown in FIG. 2A, the abscissa represents the growth inhibitor concentration, and the ordinate represents the rate of microbial growth. The rate of microbial growth represents a microbial growth coefficient for a saccharified solution and indicates that the microbe is more likely to grow as the rate of microbial growth is closer to 1.

Next, an inhibitor concentration $C_{\alpha a}$ of the saccharified solution for use in the growth of the microbe is measured (ST5). High-performance liquid chromatography can be used in the measurement.

Figure 2B:
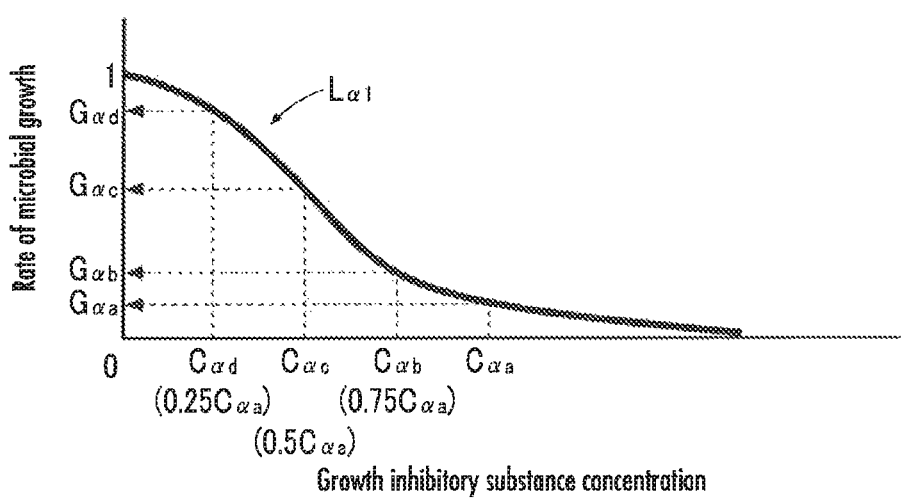

Next, as shown in FIG. 2B, the rate $G_{\alpha a}$ of microbial growth corresponding to the growth inhibitor concentration $C_{\alpha a}$ of the saccharified solution is determined from the growth inhibition curve $L_{\alpha 1}$ obtained in ST4 (ST6).

Next, the saccharified solution ratio of a totally undiluted saccharified solution is defined as $S_a=1$. As to each of mixed saccharified solutions obtained by diluting the totally undiluted saccharified solution with molasses of sugarcane as the sugar solution in respective different added amounts, each growth inhibitor concentration $C_{\alpha b}$, $C_{\alpha c}$, $C_{\alpha d}$ . . . corresponding to the saccharified solution ratio $S_b$, $S_c$, $S_d$, . . . of each mixed saccharified solution is determined from the growth inhibition curve $L_{\alpha 1}$.

As mentioned above, the growth inhibitor concentration in the sugar solution is regarded as being zero. Therefore, when the saccharified solution ratio is, for example, $S_b=0.75$, this saccharified solution ratio means that 0.75 parts by mass of the saccharified solution having the growth inhibitor concentration $C_{\alpha a}$ is diluted by 0.25 parts by mass of the sugar solution. The growth inhibitor concentration $C_{\alpha b}$ of the mixed saccharified solution obtained at the saccharified solution ratio $S_b=0.75$ is $0.75C_{\alpha a}$ ($=0.75 \times C_{\alpha a}$).

Likewise, when the saccharified solution ratio is $S_c=0.5$ at which 0.5 parts by mass the saccharified solution is diluted with 0.5 parts by mass of the sugar solution, the growth inhibitor concentration $C_{\alpha c}$ of the obtained mixed saccharified solution is $0.5C_{\alpha a}$ ($=0.5 \times C_{\alpha a}$). Likewise, when the saccharified solution ratio is $S_d=0.25$ at which 0.25 parts by mass the saccharified solution is diluted with 0.75 parts by mass of the sugar solution, the growth inhibitor concentration $C_{\alpha d}$ of the obtained mixed saccharified solution is $0.25C_{\alpha a}$ ($=0.25 \times C_{\alpha a}$).

Specifically, the growth inhibitor concentration of the mixed saccharified solution obtained by diluting the saccharified solution with the sugar solution so as to achieve a predetermined saccharified solution ratio is equal to a value determined by multiplying the growth inhibitor concentration $C_{\alpha a}$ of the saccharified solution by the saccharified solution ratio.

Then, in FIG. 2B, the rate $G_{\alpha a}$, $G_{\alpha b}$, $G_{\alpha c}$, $G_{\alpha d}$, . . . of microbial growth in each mixed saccharified solution having the saccharified solution ratio $S_a$, $S_b$, $S_c$, $S_d$, . . . and the growth inhibitor concentration $C_{\alpha a}$, $C_{\alpha b}$, $C_{\alpha c}$, $C_{\alpha d}$, . . . is determined from the growth inhibition curve $L_{\alpha 1}$ obtained in ST4 (ST7).

Figure 3A:
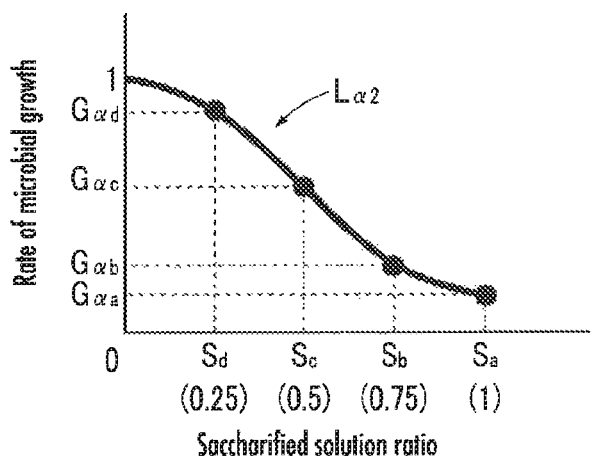

Next, as to the abscissa of the growth inhibition curve $L_{\alpha 1}$ of FIG. 2B, the growth inhibitor concentration $C_{\alpha a}$, $C_{\alpha b}$, $C_{\alpha c}$, $C_{\alpha d}$, . . . is read as the saccharified solution ratio $S_a$, $S_b$, $S_c$, $S_d$, . . . , and an overall growth inhibition curve $L_{\alpha 2}$ as a second growth inhibition curve shown in FIG. 3A is prepared from the relationship between the saccharified solution ratio $S_a$, $S_b$, $S_c$, $S_d$, . . . and the rate $G_{\alpha a}$, $G_{\alpha b}$, $G_{\alpha c}$, $G_{\alpha d}$, . . . of microbial growth (ST8).

Figure 3B:
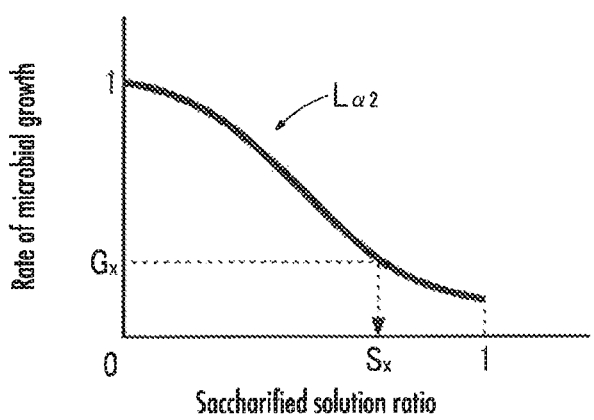

Next, as shown in FIG. 3B, a saccharified solution ratio $S_x$ corresponding to the desired rate $G_x$ of microbial growth is determined from the overall growth inhibition curve $L_{\alpha 2}$ obtained in ST8 (ST9). In this context, the desired rate $G_x$ of microbial growth is determined in consideration of the price of the sugar solution, the necessary amount of the microbe, a time required for microbial growth, energy, and cost, etc.

Next, the mixed saccharified solution is obtained by diluting the saccharified solution with molasses of sugarcane as the sugar solution such that the saccharified solution ratio $S_x$ obtained in ST9 is achieved (ST10).

In this way, the mixed saccharified solution that can enhance the growth of the microbe can be obtained without removing growth inhibitors. When the microbe is allowed to grow using the mixed saccharified solution, the rate of microbial growth is $G_x$.

In the case where the growth inhibitor α is a weakly acidic organic acid such as acetic acid or formic acid, the growth inhibitor concentration $C_{\alpha a}$ can be determined more accurately by correcting the inhibitor concentration $C_{\alpha a}$ of the saccharified solution in consideration of the acid dissociation constant of the growth inhibitor.

The correction can be carried out by multiplying the inhibitor concentration $C_{\alpha a}$ of the saccharified solution measured in ST5 by the degree of undissociation at the pH of the saccharified solution. The degree of undissociation is known to abide by the following expression:

$$\text{Degree of undissociation} = \frac{1}{1 + 10^{(pH - pKa)}}$$

In the expression, pKa represents the acid dissociation constant of the growth inhibitor in the saccharified solution. For example, the acid dissociation constant pKa of acetic acid is 4.56, and the acid dissociation constant pKa of formic acid is 3.55.

Also, the saccharified solution ratio may be determined by focusing on not only one type of growth inhibitor α but a plurality of growth inhibitors α and β contained in the saccharified solution, as described below. Hereinafter, the description about the growth inhibitor α will be omitted, and the growth inhibitor β will be mainly described.

First, in ST1, a plurality of culture media supplemented with, for example, ferulic acid, as the growth inhibitor β at respective different growth inhibitor concentrations $C_1$, $C_2$, $C_3$, . . . are prepared in the same way as in the growth inhibitor α. The microbe is cultured therein. Then, the number $N_{\beta 1}$, $N_{\beta 2}$, $N_{\beta 3}$, . . . of grown microbes at the growth inhibitor concentration $C_1$, $C_2$, $C_3$, . . . contained in each culture medium is measured.

Next, in ST2, the reference number $N_0$ of grown microbes is measured.

Next, in ST3, the rate $G_{\beta 1}$ ($G_{\beta 1}=N_{\beta 1}/N_0$), $G_{\beta 2}$, $G_{\beta 3}$, . . . of microbial growth at the growth inhibitor concentration $C_1$, $C_2$, $C_3$, . . . in each culture medium is calculated in the same way as in the growth inhibitor α.

Figure 4A:
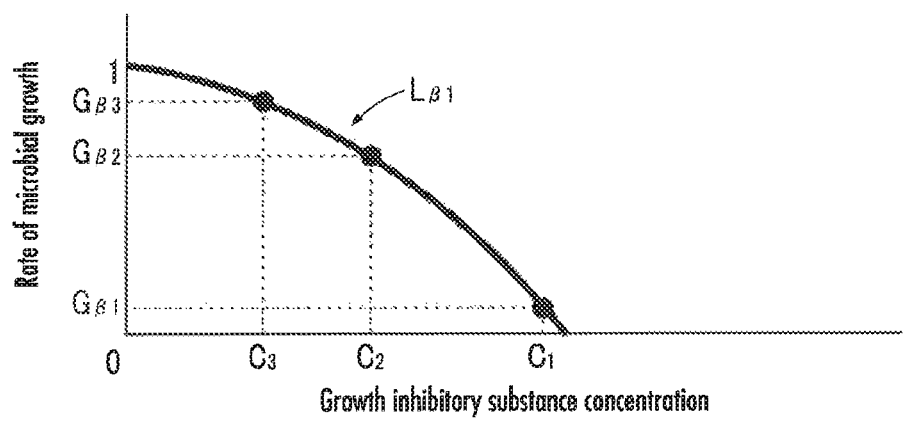

Next, in ST4, a growth inhibition curve $L_{\beta 1}$ of the growth inhibitor β shown in FIG. 4A is prepared from the relationship between each growth inhibitor concentration $C_1$, $C_2$, $C_3$, . . . and each rate $G_{\beta 1}$, $G_{\beta 2}$, $G_{\beta 3}$, . . . of microbial growth in the same way as in the growth inhibitor α.

Next, in ST5, a concentration $C_{\beta a}$ of the growth inhibitor β contained in the saccharified solution is measured in the same way as in the growth inhibitor α.

Figure 4B:
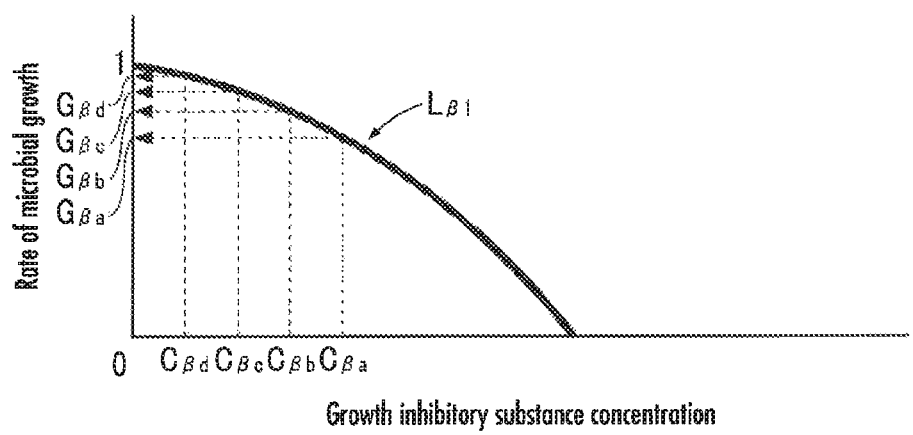

Next, in ST6, as shown in FIG. 4B, the rate $G_{\beta a}$ of microbial growth corresponding to the growth inhibitor concentration $C_{\beta a}$ of the saccharified solution is determined in the same way as in the growth inhibitor α.

Next, in ST7, first, the rate $G_{\beta a}$, $G_{\beta b}$, $G_{\beta c}$, $G_{\beta d}$, . . . of microbial growth in each mixed saccharified solution having the saccharified solution ratio $S_a$, $S_b$, $S_c$, $S_d$, . . . and the growth inhibitor concentration $C_{\beta a}$, $C_{\beta b}$, $C_{\beta c}$, $C_{\beta d}$, . . . is determined from the growth inhibition curve $L_{\beta 1}$ in the same way as in the growth inhibitor α.

Subsequently, the rate of microbial growth corresponding to the saccharified solution ratio of each mixed saccharified solution is calculated by multiplying the respective rates of microbial growth against the growth inhibitors α and β in mixed saccharified solutions having the same saccharified solution ratio. For example, the rate $G_{\alpha\beta a}$ of microbial growth at the saccharified solution ratio $S_a$ is calculated according to $G_{\alpha a} \times G_{\beta a}$. The rate $G_{\alpha\beta b}$ of microbial growth at the saccharified solution ratio $S_b$ is calculated according to $G_{\alpha b} \times G_{\beta b}$.

Figure 5A:
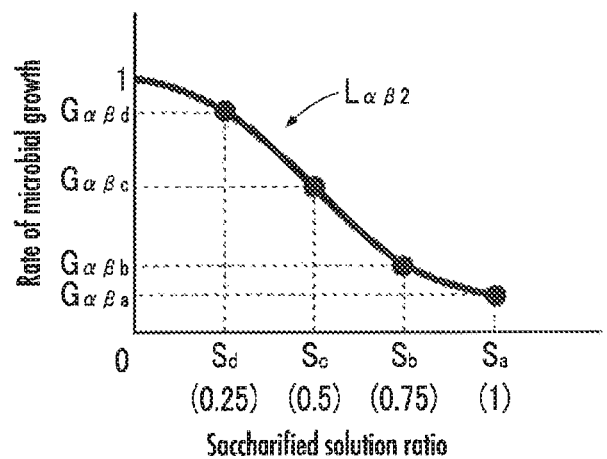

Next, in ST8, an overall growth inhibition curve $L_{\alpha\beta 2}$ shown in FIG. 5A is prepared from the relationship between the saccharified solution ratio $S_a$, $S_b$, $S_c$, $S_d$, . . . of each obtained mixed saccharified solution and the rate $G_{\alpha\beta a}$, $G_{\alpha\beta b}$, $G_{\alpha\beta c}$, $G_{\alpha\beta d}$, . . . of microbial growth.

Figure 5B:
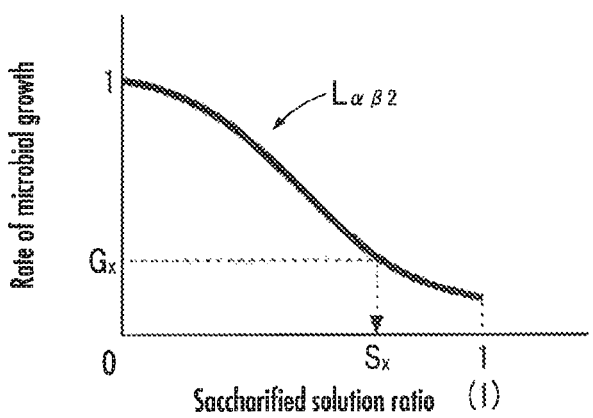

Next, in ST9, as shown in FIG. 5B, a saccharified solution ratio $S_x$ corresponding to the desired rate $G_x$ of microbial growth is determined from the overall growth inhibition curve $L_{\alpha\beta 2}$.

Next, in ST10, the mixed saccharified solution is obtained by diluting the saccharified solution with molasses of sugarcane as the sugar solution such that the saccharified solution ratio $S_x$ obtained in ST9 is achieved.

According to the method of determining the saccharified solution ratio $S_x$ by focusing on plural types of growth inhibitors α and β, the saccharified solution ratio $S_x$ can be determined more accurately as compared with the method focusing on only one type of growth inhibitor α.

In these two methods, the growth inhibitor concentration of the sugar solution is regarded as being zero, because it is much smaller than the growth inhibitor concentration of the saccharified solution and is substantially ignorable. Hence, the saccharified solution ratio $S_x$ is determined in consideration of only the growth inhibitor concentration of the saccharified solution. In contrast to this, not only the growth inhibitor concentration of the saccharified solution but the growth inhibitor concentration of the sugar solution may be taken into consideration. Here, this approach will be described with reference to the method focusing on only one type of growth inhibitor α.

First, in ST1, the sugar solution is used as the sugar solution for testing, and the microbe is cultured using a plurality of culture media in which the sugar solution is supplemented with the growth inhibitor α at respective different growth inhibitor concentrations $C_1$, $C_2$, $C_3$, . . . . Subsequently, the concentration $C_{\alpha 0}$ of the growth inhibitor α contained in the sugar solution is measured.

Next, the growth inhibitor concentration $C'_1$ ($C'_1=C_{\alpha 0}+C_1$), $C'_2$, $C'_3$, . . . contained in the culture medium is defined as the sum of the measured growth inhibitor concentration $C_{\alpha 0}$ and the concentration $C_1$, $C_2$, $C_3$, . . . of the growth inhibitor α added to the sugar solution as the sugar solution for testing. Then, the number $N_{\alpha 1}$, $N_{\alpha 2}$, $N_{\alpha 3}$, . . . of grown microbes at the growth inhibitor concentration $C'_1$, $C'_2$, $C'_3$, . . . contained in the culture medium is measured.

Thereafter, the saccharified solution ratio $S_x$ is determined in totally the same way as in ST2 to ST9 in the method of taking into consideration only the growth inhibitor concentration of the saccharified solution. Subsequently, in ST10, the mixed saccharified solution is obtained by diluting the saccharified solution with the sugar solution such that the saccharified solution ratio $S_x$ obtained in ST9 is achieved.

According to the method of taking into consideration both of the growth inhibitor concentration $C_{\alpha a}$ of the saccharified solution and the growth inhibitor concentration $C_{\alpha 0}$ of the sugar solution, the saccharified solution ratio $S_x$ can be determined further accurately as compared with the method of taking into consideration only the growth inhibitor concentration $C_{\alpha a}$ of the saccharified solution.

In the present embodiment, an overall growth inhibition curve $L_{\alpha\beta 2}$ is prepared by applying the growth inhibitor concentration $C_{\alpha a}$ of the saccharified solution to the growth inhibition curves $L_{\alpha 1}$ and $L_{\beta 1}$ prepared from the respective numbers $N_{\alpha 1}$, $N_{\alpha 2}$, $N_{\alpha 3}$, . . . and $N_{\beta 1}$, $N_{\beta 2}$, $N_{\gamma 3}$, . . . of grown microbes in the culture of the microbe. The overall growth inhibition curve $L_{\alpha\beta 2}$ represents the number of grown microbes when the microbe is allowed to grow using a mixed saccharified solution having each saccharified solution ratio.

Next, Examples will be shown as to the growth method for a microbe and the bioethanol production method of the present embodiment.

[Experiment 1. Experiment Related to Growth Method for Microbe: Examples 1 to 4]

First, by the pretreatment of lignocellulosic biomass, lignin was dissociated from the lignocellulosic biomass or the lignocellulosic biomass was swollen to obtain a pretreatment product. Milled dry corn stover was used as the lignocellulosic biomass.

For the pretreatment, first, corn stover was impregnated with dilute sulfuric acid, kept at a temperature of 150° C. or higher for 5 minutes in sealed space, and then rendered open to the atmosphere.

Next, water was added to the obtained pretreatment product. Then, its pH was adjusted to the optimum pH. After addition of cellulose- and hemicellulose-degrading enzymes in predetermined amounts, the mixture was kept at a temperature of 50° C. and stirred for 72 hours. Thereafter, a saccharified solution was obtained by removing solid matter by centrifugation.

Next, the respective growth inhibitor concentrations of acetic acid as a growth inhibitor $\alpha$, formic acid as a growth inhibitor $\beta$, furfural as a growth inhibitor $\gamma$, HMF as a growth inhibitor $\delta$, vanillin as a growth inhibitor $\epsilon$, syringaldehyde as a growth inhibitor $\zeta$, 4-hydroxyacetophenone as a growth inhibitor $\eta$, phenol as a growth inhibitor $\theta$, guaiacol as a growth inhibitor $\tau$, ferulic acid as a growth inhibitor $\kappa$, and p-coumaric acid as a growth inhibitor $\lambda$ were measured as to the obtained saccharified solution. The results are shown in Table 1. The growth inhibitor concentration $C_{\alpha 0}$ of acetic acid and the growth inhibitor concentration $C_{\beta 0}$ of formic acid are values that were not corrected with the degree of undissociation.

TABLE 1

| Growth inhibitor | Concentration (mg/L) |
| --- | --- |
| Acetic acid | $C_{\alpha 0}$: 4170 |
| Formic acid | $C_{\beta 0}$: 500 |
| Furfural | $C_{\gamma 0}$: 634 |
| HMF | $C_{\delta 0}$: 327 |
| Vanillin | $C_{\epsilon 0}$: 14 |
| Syringaldehyde | $C_{\zeta 0}$: 0 |
| 4-Hydroxyacetophenone | $C_{\eta 0}$: 3 |
| Phenol | $C_{\theta 0}$: 49 |
| Guaiacol | $C_{\tau 0}$: 0 |
| Ferulic acid | $C_{\kappa 0}$: 117 |
| p-Coumaric acid | $C_{\lambda 0}$: 181 |

On the other hand, in order to determine the saccharified solution ratio of the mixed saccharified solution of interest, culture media were prepared by adding the 11 types of growth inhibitors at various concentrations to a sugar solution for testing. The sugar solution for testing was obtained by dissolving 80 g/L glucose and 40 g/L xylose as sugars, and 10 g/L yeast extracts and 20 g/L peptone as nutrient sources for the microbe in water, and molasses of sugarcane was experimentally prepared as a sugar solution.

Next, the pH of each obtained culture medium was adjusted to 6. Then, the microbe was added thereto and cultured by stirring or shaking at a temperature of 30° C. for 20 hours. The amount of the microbe added was 0.5 in terms of a turbidity. A yeast (*Meyerozyma guilliermondii*) for Example 1, a yeast (*Saccharomyces cerevisiae*) for Example 2, a bacterium (*Escherichia coli*) for Example 3, and a bacterium (*Zymomonas mobilis*) for Example 4 was used as the microbe.

Next, the number of grown microbes resulting from the culture was measured at each growth inhibitor concentration of each of the 11 types of growth inhibitors to prepare a growth inhibition curve $L_{\alpha 1}, L_{\beta 1}, \ldots L_{\lambda 1}$.

Next, an overall growth inhibition curve $L_{\alpha\beta \ldots \lambda 2}$ was prepared from each obtained growth inhibition curve $L_{\alpha 1}, L_{\beta 1}, \ldots L_{\lambda 1}$. The obtained overall growth inhibition curve $L_{\alpha\beta \ldots \lambda 2}$ is shown in FIG. 6.

Next, the saccharified solution was diluted with the sugar solution for testing as the sugar solution to obtain mixed saccharified solutions having saccharified solution ratios 1, 0.75, 0.5, and 0.25. Since the sugar solution for testing can be regarded as having the same effects as those of molasses of sugarcane as the sugar solution, mixed saccharified solutions in which the saccharified solution is diluted with the sugar solution for testing can be regarded as being identical to mixed saccharified solutions in which the saccharified solution is diluted with molasses of sugarcane.

Next, the pH of each obtained mixed saccharified solution was adjusted to 6. Then, the yeast was added thereto at a turbidity of 0.5, kept at a temperature of 30° C., and cultured by stirring for 20 hours to allow the microbe to grow. The turbidity of the mixed saccharified solution was measured before and after the culture to calculate the rate of microbial growth. In FIG. 6, the rate of microbial growth corresponding to the saccharified solution ratio of each mixed saccharified solution is indicated by the mark ● for Example 1, by the mark ○ for Example 2, by the mark ▲ for Example 3, and by the mark ▽ for Example 4.

Table 2 shows the growth inhibitor concentrations of the mixed saccharified solutions having the saccharified solution ratios 1, 0.75, 0.5, and 0.25, and the rates of microbial growth.

TABLE 2

| Saccharified solution (part by mass) | Sugar solution (part by mass) | Saccharified solution ratio of mixed saccharified solution | Growth inhibitor concentration | Rate of microbial growth | | | |
| --- | --- | --- | --- | --- | --- | --- | --- |
| | | | | Example 1 | Example 2 | Example 3 | Example 4 |
| 1 | 0 | 1 | Equal to each growth inhibitor concentration of Table 1 | 0.13 | 0.09 | 0.01 | 0.02 |
| 0.75 | 0.25 | 0.75 | ¾ of each growth inhibitor concentration of Table 1 | 0.20 | 0.28 | 0.02 | 0.02 |
| 0.5 | 0.5 | 0.5 | ½ of each growth inhibitor concentration of Table 1 | 0.28 | 0.47 | 0.13 | 0.03 |
| 0.25 | 0.75 | 0.25 | ¼ of each growth inhibitor concentration of Table 1 | 0.38 | 0.55 | 0.28 | 0.16 |

From FIG. 6, it is evident that each overall growth inhibition curve $L_{\alpha\beta \ldots \lambda 2}$ almost agrees with each of the marks ●, ○, ▲, and ▽ and can thus be used in the determination of the saccharified solution ratio. Since the overall growth inhibition curve $L_{\alpha\beta \ldots \lambda 2}$ exhibits a larger rate of microbial growth at a smaller saccharified solution ratio of the mixed saccharified solution, it is also evident that a mixed saccharified solution in which the saccharified solution is diluted with the sugar solution can enhance the growth of the microbe.

[Experiment 2. Experiment Related to Bioethanol Production Method: Examples 5 to 7]

First, a saccharified solution was obtained in totally the same way as in Experiment 1. The concentrations of growth inhibitors contained in the saccharified solution were the same as in Table 1.

On the other hand, culture media were prepared by adding the 11 types of growth inhibitors at various concentrations to the sugar solution for testing in totally the same way as in the method of preparing culture media of Experiment 1.

Next, the pH of each obtained culture medium was adjusted to a predetermined pH. Then, a yeast (yeast of the genus *Pichia*) was added thereto as the microbe and cultured by stirring or shaking at a temperature of 30° C. for 20 hours. The pH of the culture medium was adjusted to 5 for Example 5, to 6 for Example 6, and to 4 for Example 7. The amount of the microbe added was 0.5 in terms of a turbidity in all of these examples.

Figure 7:
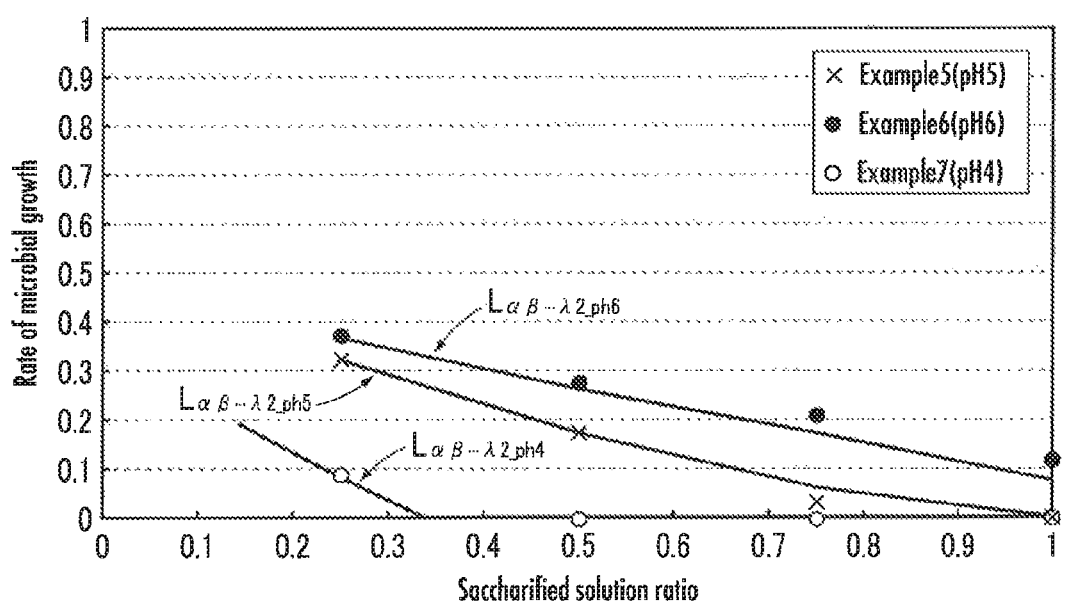
FIG. 7 is a graph showing overall growth inhibition curves $L_{\alpha\beta \ldots \lambda 2\_pH4}$, $L_{\alpha\beta \ldots \lambda 2\_pH5}$, and $L_{\alpha\beta \ldots \lambda 2\_pH6}$ of Example 7.

Next, as to the culture medium (pH 5) of Example 5, the number of grown microbes resulting from the culture was measured at each growth inhibitor concentration of each of the 11 types of growth inhibitors to prepare a growth inhibition curves $L_{\alpha 1\_pH5}$, $L_{\beta 1\_pH5}$, ... $L_{\lambda 1\_pH5}$. Then, an overall growth inhibition curve $L_{\alpha\beta \ldots \lambda 2\_pH5}$ was prepared from each of the obtained growth inhibition curves $L_{\alpha 1\_pH5}$, $L_{\beta 1\_pH5}$, ... $L_{\lambda 1\_pH5}$. The obtained overall growth inhibition curve $L_{\alpha\beta \ldots \lambda 2\_pH5}$ is shown in FIG. 7.

Next, the saccharified solution was diluted with the sugar solution for testing as the sugar solution to obtain mixed saccharified solutions having saccharified solution ratios 1, 0.75, 0.5, and 0.25. Since the sugar solution for testing can be regarded as having the same effects as those of molasses of sugarcane as the sugar solution, mixed saccharified solutions in which the saccharified solution is diluted with the sugar solution for testing can be regarded as being identical to mixed saccharified solutions in which the saccharified solution is diluted with molasses of sugarcane.

Next, the pH of each obtained mixed saccharified solution was adjusted to 5. Then, the yeast was added thereto at a turbidity of 0.5, kept at a temperature of 30° C., and cultured by stirring for 20 hours to obtain an aqueous ethanol solution. The turbidity of the mixed saccharified solution was measured before and after the culture to calculate the rate of microbial growth. In FIG. 7, the rate of microbial growth corresponding to the saccharified solution ratio of each mixed saccharified solution is indicated by the mark X.

Next, the ethanol concentration of the obtained aqueous ethanol solution was measured by gas chromatography.

Table 2 shows the growth inhibitor concentrations of the mixed saccharified solutions having the saccharified solution ratios 1, 0.75, 0.5, and 0.25, the rates of microbial growth, and the ethanol concentrations.

TABLE 2

| Saccharified solution (part by mass) | Sugar solution (part by mass) | Saccharified solution ratio of mixed saccharified solution | Growth inhibitor concentration | Rate of microbial growth | Ethanol concentration (g/L) |
|---|---|---|---|---|---|
| 1 | 0 | 1 | Equal to each growth inhibitor concentration of Table 1 | 0 | 0 |
| 0.75 | 0.25 | 0.75 | ¾ of each growth inhibitor concentration of Table 1 | 0.02 | 0 |
| 0.5 | 0.5 | 0.5 | ½ of each growth inhibitor concentration of Table 1 | 0.18 | 27 |
| 0.25 | 0.75 | 0.25 | ¼ of each growth inhibitor concentration of Table 1 | 0.32 | 36 |

From FIG. 7, it is evident that the overall growth inhibition curve $L_{\alpha\beta \ldots \lambda 2\_pH5}$ almost agrees with the mark X and can thus be used in the determination of the saccharified solution ratio. Since the overall growth inhibition curve $L_{\alpha\beta \ldots \lambda 2\_pH5}$ exhibits a larger rate of microbial growth at a smaller saccharified solution ratio of the mixed saccharified solution, it is also evident that a mixed saccharified solution in which the saccharified solution is diluted with the sugar solution can avoid inhibiting the growth of the microbe.

From Table 2, it is evident that, as the saccharified solution ratio of the mixed saccharified solution is decreased, the rate of microbial growth is increased and the ethanol concentration obtained by the fermentation of the mixed saccharified solution is increased.

Next, as to the culture medium (pH 6) of Example 6 and the culture medium (pH 4) of Example 7, overall growth inhibition curves $L_{\alpha\beta \ldots \lambda 2\_pH6}$ and $L_{\alpha\beta \ldots \lambda 2\_pH4}$ were prepared in totally the same way as in Example 5. The obtained overall growth inhibition curves $L_{\alpha\beta \ldots \lambda 2\_pH6}$ and $L_{\alpha\beta \ldots \lambda 2\_pH4}$ are shown in FIG. 7.

Next, aqueous ethanol solutions were obtained in totally the same way as in Example 5 except that the mixed saccharified solutions having the saccharified solution ratios 1, 0.75, 0.5, and 0.25 were cultured at pH 6 and pH 4, respectively. In FIG. 7, the rate of microbial growth corresponding to the saccharified solution ratio of each mixed saccharified solution is indicated by the mark ● for Example 6 and by the mark ○ for Example 7.

From FIG. 7, it is evident that the overall growth inhibition curves $L_{\alpha\beta \ldots \lambda 2\_pH6}$ and $L_{\alpha\beta \ldots \lambda 2\_pH4}$ almost agree with the marks ● and ○, respectively, and can thus be used in the determination of the saccharified solution ratio of the mixed saccharified solution of interest.

What is claimed is:

1. A growth method for a microbe in a saccharified solution containing a saccharification product, comprising steps of:
    obtaining a mixed saccharified solution by diluting the saccharified solution containing a growth inhibitor which inhibits the growth of the microbe with a sugar solution having a smaller growth inhibitor concentration than that of the saccharified solution such that the growth inhibitor concentration is decreased; and
    allowing the microbe to grow by adding the microbe to the mixed saccharified solution,
    wherein obtaining the mixed saccharified solution comprises:

a first step of culturing the microbe using a plurality of culture media in which, with respect to each growth inhibitor of a plurality of growth inhibitors contained in the saccharified solution, a sugar solution for testing is supplemented with the growth inhibitor at respective different growth inhibitor concentrations, and measuring a number of grown microbes for each of the growth inhibitor concentration contained in each culture medium with respect to each growth inhibitor;

a second step of culturing the microbe using the sugar solution for testing unsupplemented with each growth inhibitor as a culture medium, and measuring a number of grown microbes in the unsupplemented sugar solution for testing to prepare a reference number of grown microbes;

a third step of calculating a rate of microbial growth at each growth inhibitor concentration with respect to each growth inhibitor by dividing the number of grown microbes for each of the growth inhibitor concentration with respect to each growth inhibitor by the reference number of grown microbes;

a fourth step of preparing a first growth inhibition curve from a relationship between the growth inhibitor concentration of each culture medium and the rate of microbial growth with respect to each growth inhibitor;

a fifth step of measuring each growth inhibitor concentration of the saccharified solution;

a sixth step of determining the rate of microbial growth corresponding to the growth inhibitor concentration of the saccharified solution with respect to each growth inhibitor from the first growth inhibition curve with respect to each growth inhibitor;

a seventh step of, as to each of the mixed saccharified solutions in which the saccharified solution in an undiluted state is diluted with the sugar solution in respective different amounts, determining the rate of microbial growth corresponding to a saccharified solution ratio of each mixed saccharified solution with respect to each growth inhibitor from the first growth inhibition curve of each growth inhibitor, when the saccharified solution ratio of the undiluted saccharified solution is defined as 1, and then calculating the rate of microbial growth corresponding to the saccharified solution ratio of each mixed saccharified solution by multiplying the respective rates of microbial growth of each of the growth inhibitors in the mixed saccharified solutions having the same saccharified solution ratio;

an eighth step of preparing a second growth inhibition curve from a relationship between the saccharified solution ratio of each mixed saccharified solution and the rate of microbial growth;

a ninth step of determining a saccharified solution ratio corresponding to a desired rate of microbial growth from the second growth inhibition curve; and a tenth step of obtaining the mixed saccharified solution by diluting the saccharified solution with the sugar solution such that the saccharified solution ratio obtained in the ninth step is achieved.

2. The growth method for a microbe according to claim 1, wherein
the saccharified solution is a saccharified solution containing a saccharification product obtained by saccharifying, with a saccharifying enzyme, a pretreatment product resulting from a pretreatment of lignocellulosic biomass.

3. The growth method for a microbe according to claim 1, wherein
the saccharified solution contains one or more sugars selected from a group consisting of glucose, xylose, and arabinose.

4. The growth method for a microbe according to claim 1, wherein
the sugar solution is one or more types of liquids selected from a group consisting of molasses of sugarcane, juice of sugarcane, a concentrate of the juice of sugarcane, a liquid of saccharified rice, a liquid of saccharified wheat, and a liquid of saccharified corn.

5. The growth method for a microbe according to claim 1, wherein
the microbe is one or more microbes selected from a group consisting of a bacterium, a fungus, and an alga.

6. The growth method for a microbe according to claim 5, wherein
the bacterium is one or more microbes selected from a group consisting of *Zymomonas mobilis*, *Zymobacter palmae*, *Clostridium phytofermentans*, *Clostridium thermocellum*, *Clostridium beijerinckii*, and *Clostridium acetobutylicum*, *Moorella thermoacetica*, *Escherichia coli*, *Klebsiella oxytoca*, *Thermoanaerobacterium saccharolyticum*, *Bacillus subtilis*, and *Corynebacterium glutamicum*.

7. The growth method for a microbe according to claim 5, wherein
the fungus is one or more microbes selected from a group consisting of: one or more yeasts selected from a group consisting of *Saccharomyces cerevisiae*, *Saccharomyces monacensis*, *Saccharomyces bayanus*, *Saccharomyces pastorianus*, *Saccharomyces carlsbergensis*, *Saccharomyces pombe*, *Kluyveromyces marxiamus*, *Kluyveromyces lactis*, *Kluyveromyces fragilis*, *Pichia stipitis*, *Candida shehatae*, *Candida tropicalis*, *Meyerozyma guilliermondii*, *Rhodosporidium toruloides*, *Lipomyces starkyei*, *Yarrowia lipolytica*, *Sporotrichum thermophile*, *Myceliophthora thermophila*, *Neurospora crassa*, *Cryptococcus curvatus*; and a *filamentous fungus*.

8. The growth method for a microbe according to claim 5, wherein
the alga is one or more microbes selected from a group consisting of *Aurantiochytrium*, *Nannochloropsis*, *Schizochytrium*, *Nannochloris*, *Stichococcus*, *Neochloris oleoabundans*, *Chlorella*, *Dunaliella*, *Botryococcus braunii*, *Scenedesmus*, *Hantzschia*.

9. The growth method for a microbe according to claim 1, wherein
the growth inhibitor in the saccharified solution is one or more compounds selected from a group consisting of an organic acid, a compound having an aldehyde group, a compound having a ketone group, a compound having a phenol group, and melanoidin.

10. The growth method for a microbe according to claim 9, wherein
the organic acid is one or more compounds selected from a group consisting of acetic acid, formic acid, p-coumaric acid, ferulic acid, and benzoic acid.

11. The growth method for a microbe according to claim 9, wherein
the compound having an aldehyde group is one or more compounds selected from a group consisting of furfural, 5-hydroxymethylfurfural, vanillin, syringaldehyde, and 4-hydroxyacetophenone.

12. The growth method for a microbe according to claim 9, wherein the compound having a phenol group is one or more compounds selected from a group consisting of phenol and guaiacol.

13. The growth method for a microbe according to claim 9, wherein
the saccharified solution contains at least acetic acid as the growth inhibitor, and
the tenth step of obtaining the mixed saccharified solution comprises diluting the saccharified solution such that a concentration of an undissociated form of the acetic acid is 700 mg/L or lower.

14. The growth method for a microbe according to claim 9, wherein
the saccharified solution contains at least furfural as the growth inhibitor, and
the tenth step of obtaining the mixed saccharified solution comprises diluting the saccharified solution such that a concentration of the furfural is 700 mg/L or lower.

15. The growth method for a microbe according to claim 9, wherein
the saccharified solution contains at least p-coumaric acid as the growth inhibitor, and
the tenth step of obtaining the mixed saccharified solution comprises diluting the saccharified solution such that a concentration of the p-coumaric acid is 500 mg/L or lower.

16. The growth method for a microbe according to claim 1, wherein
the step of allowing the microbe to grow comprises adjusting a pH of the mixed saccharified solution to a range of 4 to 7 before adding the microbe to the mixed saccharified solution.

17. The growth method for a microbe according to claim 1, wherein
the first step employs the sugar solution as the sugar solution for testing and comprises measuring a growth inhibitor concentration of the sugar solution, and defining the growth inhibitor concentration of the culture medium as a sum of the measured growth inhibitor concentration and the concentration of the growth inhibitor added to the sugar solution as the sugar solution for testing.

18. A bioethanol production method of saccharifying, with a saccharifying enzyme, a pretreatment product resulting from the pretreatment of lignocellulosic biomass, and fermenting the obtained saccharified solution with a microbe to form ethanol, the method comprising steps of:
obtaining a mixed saccharified solution by diluting the saccharified solution containing a growth inhibitor which inhibits growth of the microbe with a sugar solution having a smaller growth inhibitor concentration than that of the saccharified solution such that the growth inhibitor concentration is decreased; and
fermenting the mixed saccharified solution with the microbe to form ethanol,
wherein obtaining the mixed saccharified solution comprises:
a first step of culturing the microbe using a plurality of culture media in which, with respect to each growth inhibitor of a plurality of growth inhibitors contained in the saccharified solution a sugar solution for testing is supplemented with the growth inhibitor at respective different growth inhibitor concentrations, and measuring a number of grown microbes for each of the growth inhibitor concentration contained in each culture medium with respect to each growth inhibitor;
a second step of culturing the microbe using the sugar solution for testing unsupplemented with each growth inhibitor as a culture medium, and measuring a number of grown microbes in the unsupplemented sugar solution for testing to prepare a reference number of grown microbes;
a third step of calculating a rate of microbial growth at each growth inhibitor concentration with respect to each growth inhibitor by dividing the number of grown microbes for each of the growth inhibitor concentration with respect to each growth inhibitor by the reference number of grown microbes;
a fourth step of preparing a first growth inhibition curve from a relationship between the growth inhibitor concentration of each culture medium and the rate of microbial growth with respect to each growth inhibitor;
a fifth step of measuring each growth inhibitor concentration of the saccharified solution;
a sixth step of determining the rate of microbial growth corresponding to the growth inhibitor concentration of the saccharified solution with respect to each growth inhibitor from the first growth inhibition curve with respect to each growth inhibitor;
a seventh step of, as to each of the mixed saccharified solutions in which the saccharified solution in an undiluted state is diluted with the sugar solution in respective different amounts, determining the rate of microbial growth corresponding to a saccharified solution ratio of each mixed saccharified solution with respect to each growth inhibitor from the first growth inhibition curve of each growth inhibitor, when the saccharified solution ratio of the undiluted saccharified solution is defined as 1, and then calculating the rate of microbial growth corresponding to the saccharified solution ratio of each mixed saccharified solution by multiplying the respective rates of microbial growth of each of the growth inhibitors in the mixed saccharified solutions having the same saccharified solution ratio;
an eighth step of preparing a second growth inhibition curve from a relationship between the saccharified solution ratio of each mixed saccharified solution and the rate of microbial growth;
a ninth step of determining a saccharified solution ratio corresponding to a desired rate of microbial growth from the second growth inhibition curve; and
a tenth step of obtaining the mixed saccharified solution by diluting the saccharified solution with the sugar solution such that the saccharified solution ratio obtained in the ninth step is achieved.

19. The bioethanol production method according to claim 18, wherein
the saccharified solution contains one or more sugars selected from a group consisting of glucose, xylose, and arabinose.

20. The bioethanol production method according to claim 18, wherein
the sugar solution is one or more types of liquids selected from a group consisting of molasses of sugarcane, juice of sugarcane, a concentrate of the juice of sugarcane, a liquid of saccharified rice, a liquid of saccharified wheat, and a liquid of saccharified corn.

21. The bioethanol production method according to claim 18, wherein
the microbe is one or more microbes selected from a group consisting of a yeast, *Zymomonas*, *Zymobacter*, *Corynebacterium*, and *Escherichia coli*.

22. The bioethanol production method according to claim 18, wherein
the growth inhibitor in the saccharified solution is one or more compounds selected from a group consisting of an organic acid, a compound having an aldehyde group, a compound having a ketone group, a compound having a phenol group, and melanoidin.

23. The bioethanol production method according to claim 22, wherein
the organic acid is one or more compounds selected from a group consisting of acetic acid, formic acid, p-coumaric acid, ferulic acid, and benzoic acid.

24. The bioethanol production method according to claim 22, wherein
the compound having an aldehyde group is one or more compounds selected from a group consisting of furfural, 5-hydroxymethylfurfural, vanillin, syringaldehyde, and 4-hydroxyacetophenone.

25. The bioethanol production method according to claim 22, wherein
the compound having a phenol group is one or more compounds selected from a group consisting of phenol and guaiacol.

26. The bioethanol production method according to claim 22, wherein
the saccharified solution contains at least acetic acid as the growth inhibitor, and
the tenth step of obtaining the mixed saccharified solution comprises diluting the saccharified solution such that a concentration of an undissociated form of the acetic acid is 700 mg/L or lower.

27. The bioethanol production method according to claim 22, wherein
the saccharified solution contains at least furfural as the growth inhibitor, and
the tenth step of obtaining the mixed saccharified solution comprises diluting the saccharified solution such that a concentration of the furfural is 700 mg/L or lower.

28. The bioethanol production method according to claim 22, wherein
the saccharified solution contains at least p-coumaric acid as the growth inhibitor, and
the tenth step of obtaining the mixed saccharified solution comprises diluting the saccharified solution such that a concentration of the p-coumaric acid is 500 mg/L or lower.

29. The bioethanol production method according to claim 18, wherein
the step of allowing the microbe to grow comprises adjusting a pH of the mixed saccharified solution to a range of 4 to 7 before adding the microbe to the mixed saccharified solution.

30. The bioethanol production method according to claim 18, wherein
the first step employs the sugar solution as the sugar solution for testing and comprises measuring a growth inhibitor concentration of the sugar solution, and defining the growth inhibitor concentration of the culture medium as a sum of the measured growth inhibitor concentration and the concentration of the growth inhibitor added to the sugar solution as the sugar solution for testing.

31. The growth method for a microbe according to claim 1, wherein the microbe is one or more microbes selected from a group consisting of prokaryotic microorganisms and eukaryotic microorganisms.

\* \* \* \* \*